US011266760B2

(12) United States Patent
Lim et al.

(10) Patent No.: US 11,266,760 B2
(45) Date of Patent: Mar. 8, 2022

(54) CARTRIDGE AND STERILIZING DEVICE USING SAME

(71) Applicant: PLASMAPP CO., LTD., Daejeon (KR)

(72) Inventors: Youbong Lim, Daejeon (KR); Seunghun Lee, Seoul (KR); Junyoung Kim, Daejeon (KR); Miseon Hwang, Daejeon (KR)

(73) Assignee: PLASMAPP CO., LTD., Daejeon (KR)

( * ) Notice: Subject to any disclaimer, the term of this patent is extended or adjusted under 35 U.S.C. 154(b) by 167 days.

(21) Appl. No.: 16/607,973

(22) PCT Filed: Apr. 23, 2018

(86) PCT No.: PCT/KR2018/004683
§ 371 (c)(1),
(2) Date: Oct. 24, 2019

(87) PCT Pub. No.: WO2018/199574
PCT Pub. Date: Nov. 1, 2018

(65) Prior Publication Data
US 2021/0100921 A1    Apr. 8, 2021

(30) Foreign Application Priority Data

Apr. 25, 2017  (KR) .................. 10-2017-0052738
Apr. 17, 2018  (KR) .................. 10-2018-0044472

(51) Int. Cl.
*A61L 2/26* (2006.01)
*A61L 2/20* (2006.01)
*G06K 7/14* (2006.01)

(52) U.S. Cl.
CPC .............. *A61L 2/26* (2013.01); *A61L 2/20* (2013.01); *A61L 2/206* (2013.01); *A61L 2/208* (2013.01);
(Continued)

(58) Field of Classification Search
CPC ... A61L 2/16; A61L 2/18; A61L 2/183; A61L 2/186; A61L 2/20; A61L 2/208;
(Continued)

(56) References Cited

U.S. PATENT DOCUMENTS

| 4,642,165 A | 2/1987 | Bier |
| 4,941,518 A * | 7/1990 | Williams .................. A61L 2/18 141/1 |

(Continued)

FOREIGN PATENT DOCUMENTS

| EP | 3533474 A1 | 9/2019 |
| JP | 2015-116497 A | 6/2015 |

(Continued)

OTHER PUBLICATIONS

Partial Supplementary European Search Report dated Dec. 23, 2020 from the European Patent Office in Application No. 18790219.2.
(Continued)

*Primary Examiner* — Timothy C Cleveland
(74) *Attorney, Agent, or Firm* — Sughrue Mion, PLLC

(57) ABSTRACT

The present invention provides a cartridge used for a sterilization device. The cartridge comprises a sterilant container configured to contain a sterilant used for sterilization and an injector receiving the sterilant contained in the sterilant container through the sterilization device and delivering the sterilant to an article to be sterilized.

30 Claims, 19 Drawing Sheets

(52) U.S. Cl.
CPC ......... *G06K 7/1413* (2013.01); *G06K 7/1417* (2013.01); *A61L 2202/11* (2013.01); *A61L 2202/123* (2013.01); *A61L 2202/15* (2013.01); *A61L 2202/181* (2013.01)

(58) Field of Classification Search
CPC .......... A61L 2/24; A61L 2/26; A61L 2202/10; A61L 2202/11; A61L 2202/12; A61L 2202/123; A61L 2202/15; A61L 2202/181
See application file for complete search history.

(56) References Cited

U.S. PATENT DOCUMENTS

| 6,132,680 A | 10/2000 | Addy et al. |
| 2006/0280646 A1 | 12/2006 | Shiosawa |
| 2014/0170020 A1 | 6/2014 | Hiruta |

FOREIGN PATENT DOCUMENTS

| KR | 2001-0104380 A | 11/2001 |
| KR | 2002-0077887 A | 10/2002 |
| KR | 10-2007-0006694 A | 1/2007 |
| KR | 10-1224842 B1 | 1/2013 |
| KR | 10-1273764 B1 | 6/2013 |
| KR | 10-201-0051202 A | 5/2015 |
| KR | 10-2015-0051202 A | 5/2015 |
| KR | 10-2017-0017023 A | 2/2017 |
| WO | 93/17726 A1 | 9/1993 |
| WO | 03/068274 A2 | 8/2003 |

OTHER PUBLICATIONS

The Extended European Search Report dated Mar. 24, 2021, issued by the European Patent Office in application No. 18790219.2.
International Search Report for PCT/KR2018/004683 dated Oct. 17, 2018 (PCT/ISA/210).
Korean Notification of Reason for Refusal for 10-2017-0052738 dated Nov. 2, 2018.

\* cited by examiner

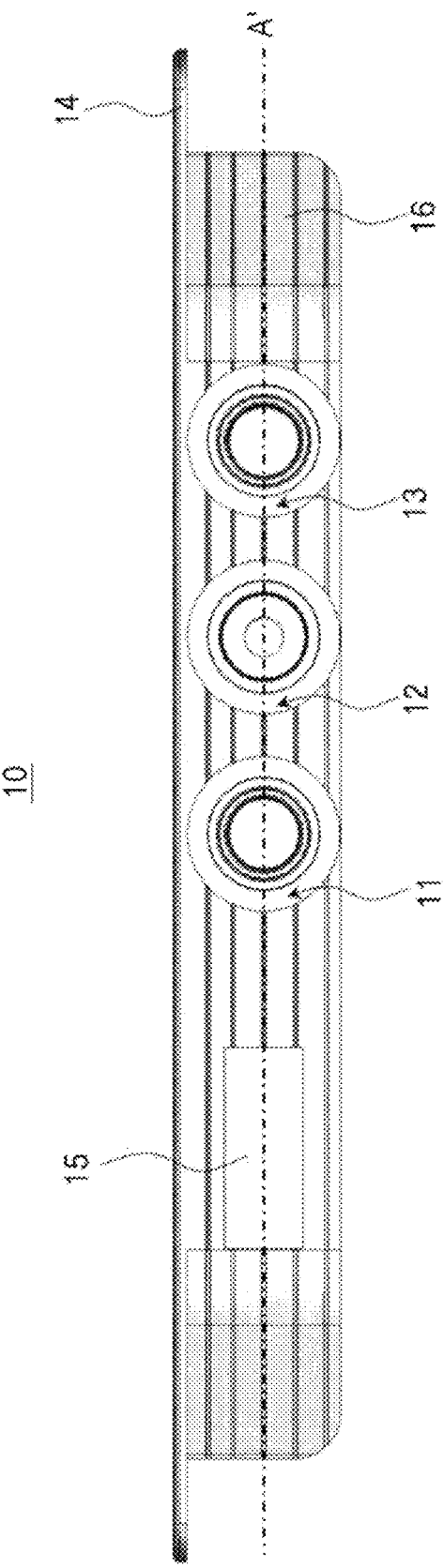

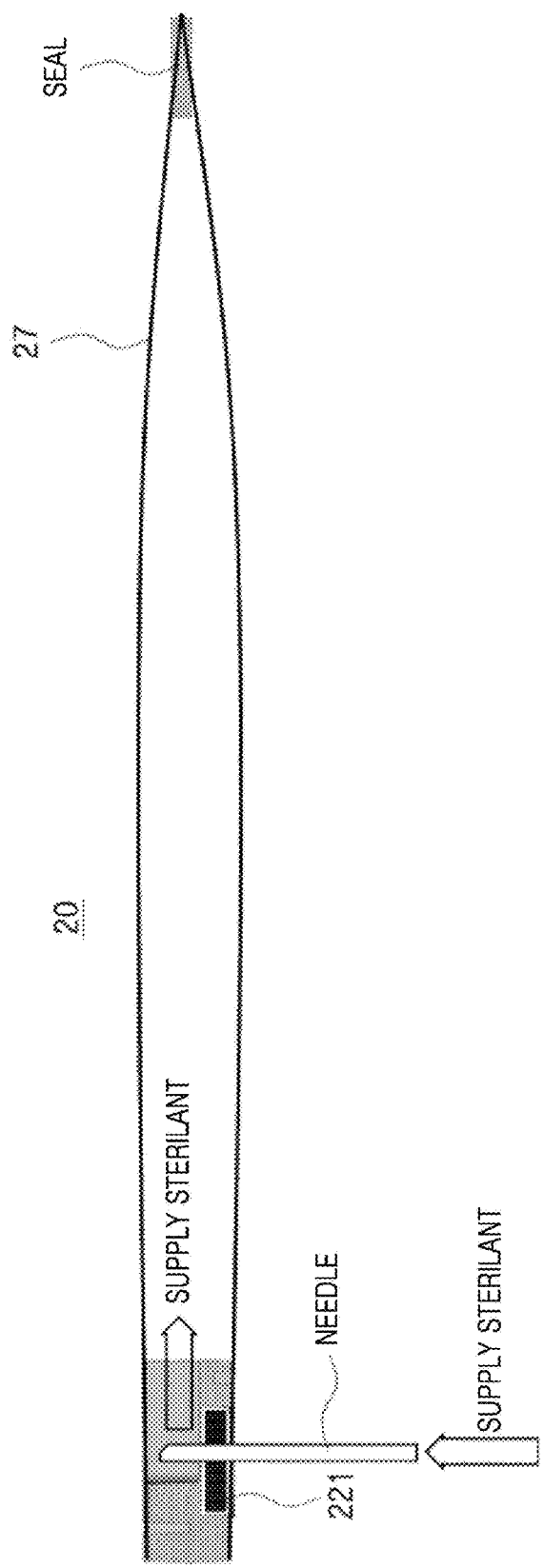

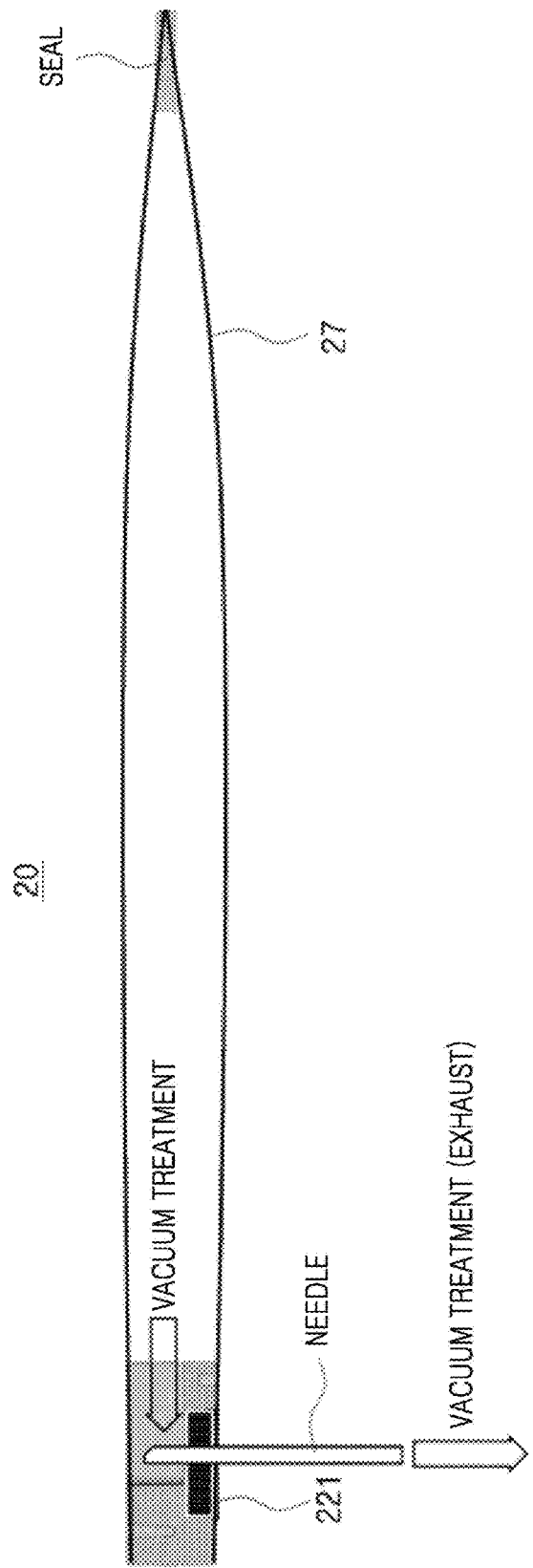

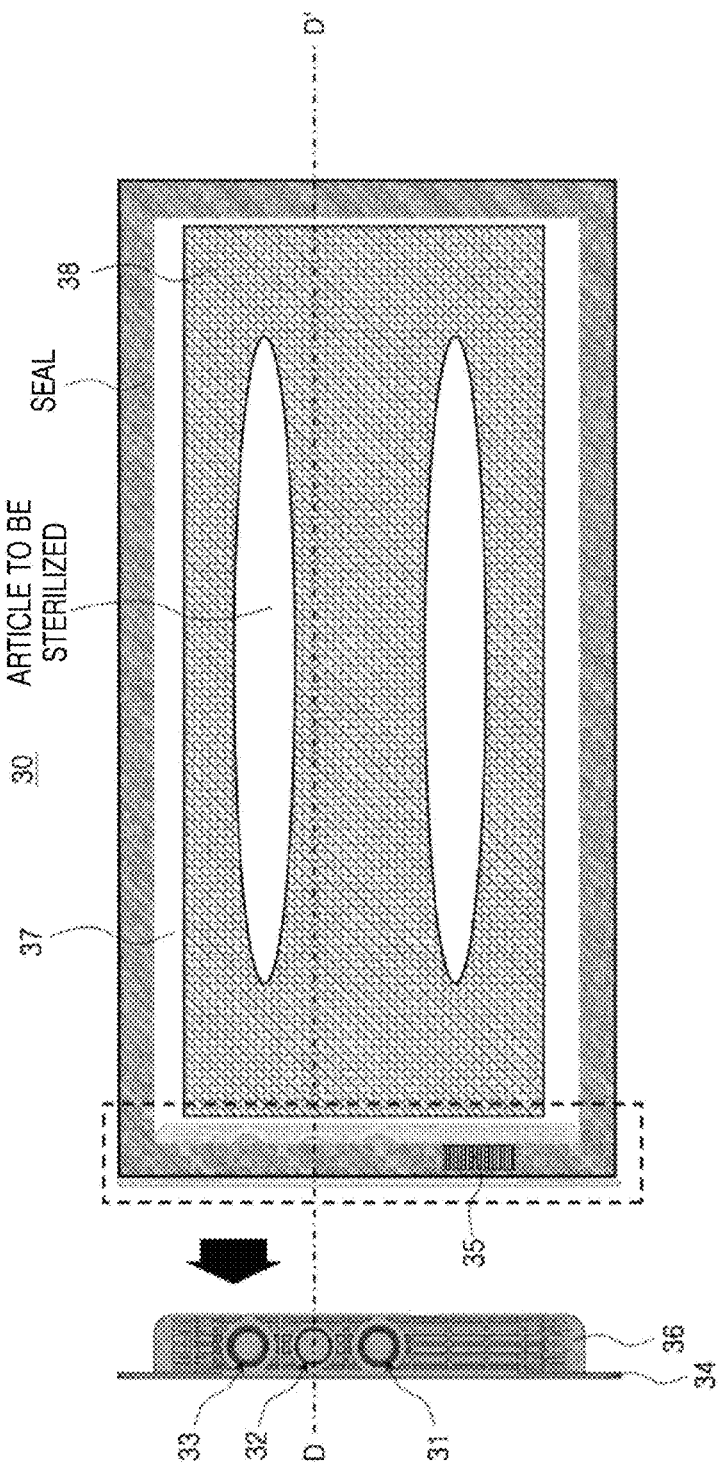

CARTRIDGE AND STERILIZING DEVICE USING SAME

TECHNICAL FIELD

The present disclosure relates to a sterilization device, and more particularly, to a cartridge having a sterilant container and an injector and a sterilization device using the cartridge.

BACKGROUND ART

A chemical sterilizer is a device that performs a sterilization process at a low temperature by using a gas such as hydrogen peroxide ($H_2O_2$), ethylene oxide ($C_2H_4O$), chlorine dioxide ($ClO_2$) as a sterilant.

Conventional chemical sterilizers using hydrogen peroxide as a sterilant decompress the interior of a sterilization chamber to 10 Torr or less to form basic vacuum pressure and supply a sterilant. In such vacuum conditions, the sterilant may be vaporized at relatively low temperatures (e.g., 60° C.).

For sterilization, the vaporized sterilant needs to be supplied into a certain volume of the chamber. Here, the amount of sterilant to be supplied needs to be adjusted so that the sterilant is at or below the maximum pressure (maximum vapor pressure) that can be maintained in a gaseous state at a set temperature. As such, the sterilant needs to be maintained in the gaseous state to be delivered to and within an article to be sterilized in the chamber and a successful sterilization process may be performed.

Conventional chemical sterilizers have sterilization chambers of several tens of liters or more, and the amount of sterilant that can be supplied to a chamber of this volume is on the order of several milliliters in an environment of about 55° C. When a sterilant is injected above vapor pressure, partial condense occurs in the sterilization chamber. As a result, the sterilant may not be sufficiently delivered to the article to be sterilized, so that sterilization may not be performed properly. In addition, when a sterilant having such a high oxidizing property is condensed in or on the surface of the article to be sterilized, since the sterilant may remain on the article to be sterilized even after the sterilization process, it is difficult to secure safety of the sterilization process because the sterilant is likely to be exposed to a user.

Meanwhile, when a sterilant is not sufficiently injected, since a sterilant concentration in the sterilization chamber is lowered, sterilization is difficult to be achieved at a required level due to a sterilization efficiency being lowered. Supplying a fixed amount of sterilant is required to ensure the reliability and safety of the sterilization process.

In order to solve such a problem, in the conventional chemical sterilizer, an appropriate amount of sterilant is supplied to a chamber by using a method of controlling a vaporization temperature of a vaporizer to vaporize a sterilant and the amount of heat applied to the vaporizer. For example, in U.S. Pat. No. 4,642,165, a method in which a sterilant is discharged at a predetermined constant flow rate and vaporized through a heating surface, but heat is applied to the heating surface by the amount of heat in which the sterilant is vaporized is used, and thus, the sterilant may be discharged and vaporized at the same time.

However, in order to use such a method, a device for constantly discharging a sterilant and a vaporizer having a complicated structure connected thereto are required, so that the above method has a problem that it is difficult to apply to a small sterilization device. In addition, since the sterilization device according to the above patent should be provided with a separate space for storing a sterilant, it is more difficult to miniaturize and a path of the sterilant is relatively longer, so that in the case of a chemically unstable sterilant, the sterilant is decomposed and the effect of the sterilant is reduced.

Meanwhile, conventional chemical or plasma sterilizers, to prevent reinfection after sterilization, use a sterilization method in a state in which an article to be sterilized is packaged in a permeable pouch. In order for the sterilization method to be effective, a sterilant needs to be introduced into the pouch, so that one side or a specific portion of the pouch is manufactured using a film having selective permeability. TIVEK® is generally used as a film having selective permeability. As such, the conventional sterilizer performs a sterilization process by transmitting a sterilant using a selective permeable film, and prevents the permeation of bacteria to maintain sterility after the sterilization process. For example, U.S. Pat. No. 6,132,680 discloses a pouch with a port having selective permeability as one of its embodiments.

A sterilization device using such a pouch has the advantage of preventing an article to be sterilized from being infected again after sterilization, but since a sterilant is difficult to be sufficiently introduced into the pouch, it takes a lot of time to sterilize, and the sterilization effect is inevitably deteriorated. Furthermore, due to the low thermal conductivity of a film constituting the pouch, it is difficult to ensure temperature uniformity of the surface and inside of the film, and there is a problem in that the sterilant is condensed on a specific portion of the pouch. When the sterilant is condensed, the article to be sterilized is difficult to be sterilized evenly, and after the end of sterilization the sterilant is more likely to remain, which may pose a threat to user's safety.

In order to solve the above problems, KR 10-2017-0017023A discloses a method of sterilizing by directly injecting a sterilant generated through plasma generation inside a vacuum wrapper. However, such a method does not provide sufficient sterilization performance, but has to generate a sterilant through plasma generation, and thus, the device is complicated and thus is difficult to apply to a small sterilization device.

The present disclosure provides, in order to solve the above conventional problems, a cartridge capable of containing a sterilant and a sterilization device using the cartridge.

DESCRIPTION OF EMBODIMENTS

Technical Problem

The present disclosure is directed to a cartridge and a sterilization device using the same capable of reducing a distance at which a sterilant is supplied to a chamber or a packaging pouch so that a chemical property of the sterilant does not change when sterilization occurs by using a method of supplying an appropriate amount of sterilant into the chamber or the packaging pouch using the cartridge having a sterilant container, and vaporizing a sterilant contained in the sterilant container in the sterilization device.

The present disclosure is further directed to a cartridge and a sterilization device using the same capable of forming a packaging pouch coupled to the cartridge from a material which is not permeable to a sterilant and a material having high thermal conductivity, to prevent condensation of the sterilant and achieve a high sterilization efficiency.

The present disclosure is further directed to a cartridge and a sterilization device using the same which are provided with a tag such as a bar code or a QR code for checking information about the cartridge or the packaging pouch, so that the use, authenticity, and aligned state of the cartridge may be checked.

The present disclosure is further directed to a cartridge and a sterilization device using the same which are provided with a tray inside a packaging pouch to secure a space where a sterilant can be diffused even if the outside of the packaging pouch is not decompressed, so that even a small vacuum pump may achieve efficient sterilization.

As described above, the main technical problem to be solved by the present disclosure has been described, but the technical problem of the present disclosure is not limited thereto, and the technical problem which one of ordinary skill in the art can understand or acquire from the whole of this specification also corresponds to the technical problem of the present disclosure.

Solution to Problem

According to an aspect of the present disclosure a cartridge used for a sterilization device, the cartridge comprises a sterilant container configured to contain a sterilant used for sterilization; and an injector receiving the sterilant contained in the sterilant container through the sterilization device and delivering the sterilant to an article to be sterilized.

According to an example embodiment, the cartridge further comprises a coupling portion coupled to the sterilization device to induce the cartridge to be aligned in a certain position.

According to an example embodiment, the cartridge further comprises a packaging pouch coupled to one end of the cartridge and containing the article to be sterilized.

According to an example embodiment, the packaging pouch comprises a material that does not permeate gas or liquid to maintain airtightness.

According to an example embodiment, at least one surface of the packaging pouch comprises a heat conductive material.

According to an example embodiment, the cartridge further comprises a tag such as a bar code or QR code for checking information about the cartridge on one side of the packaging pouch.

According to an example embodiment, the cartridge further comprises a tray, located in the packaging pouch, for securing a space inside the packaging pouch.

According to an example embodiment, the sterilant container or the injector is sealed with an elastic material.

According to an example embodiment, the injector further comprises a path for decompressing the inside of the packaging pouch or supplying a sterilant into the packaging pouch.

According to an example embodiment, the cartridge further comprises a tag such as a bar code or QR code for checking information about the cartridge on one side of the cartridge.

According to an example embodiment, the sterilant container or the injector is sealed with an elastic material.

According to an aspect of the present disclosure a cartridge used for a sterilization device, the cartridge comprises a sterilant container configured to contain a sterilant used for sterilization; an injector receiving the sterilant contained in the sterilant container through the sterilization device and delivering the sterilant to an article to be sterilized; a coupling portion coupled to the sterilization device to induce the cartridge to be aligned in a certain position; and a packaging pouch containing an article to be sterilized, wherein the packaging pouch comprises a film that does not permeate gas or liquid, and one end of the packaging pouch is coupled to the cartridge so as to remain sealed.

According to an aspect of the present disclosure a sterilization device comprising a cartridge, a sterilant extractor, and a sterilant provider, wherein the cartridge comprises a sterilant container configured to contain a sterilant used for sterilization; an injector receiving the sterilant contained in the sterilant container through the sterilization device and delivering the sterilant to an article to be sterilized; and a coupling portion coupled to the sterilization device to induce the cartridge to be aligned in a certain position, wherein the sterilant extractor extracts the sterilant contained in the sterilant container and delivers the sterilant to the sterilant provider, and the sterilant provider provides the sterilant received from the sterilant extractor to the injector.

According to an example embodiment, the sterilization device further comprises a tag such as a bar code or QR code for checking information about the cartridge on one side of the cartridge.

According to an example embodiment, information about the tag is used to check whether the cartridge is in a coupled state, used, and genuine.

According to an example embodiment, the sterilant container or the injector is sealed with an elastic material.

According to an example embodiment, the sterilization device further comprises a coupling container coupled to the coupling portion to induce the cartridge to be aligned in a certain position.

According to an example embodiment, the sterilant provider comprises a vaporizer for vaporizing and supplying a sterilant to the injector.

According to an example embodiment, the sterilant extractor comprises a needle for extracting a sterilant from the sterilant container, and a driver for moving the needle.

According to an example embodiment, the sterilization device further comprises a packaging pouch coupled to one end of the cartridge and containing the article to be sterilized.

According to an example embodiment, the packaging pouch comprises a material that does not permeate gas or liquid to maintain airtightness.

According to an example embodiment, at least one surface of the packaging pouch comprises a heat conductive material.

According to an example embodiment, the sterilization device further comprises a tag such as a bar code or QR code for checking information about the cartridge on one side of the packaging pouch.

According to an example embodiment, the sterilization device further comprises a tray, located in the packaging pouch, for securing a space inside the packaging pouch.

According to an example embodiment, the sterilization device further comprises a heating device heating the packaging pouch or an interior space thereof.

According to an example embodiment, the sterilization device further comprises a vacuum pump connected to the sterilant provider and decompressing the inside of the packaging pouch through the injector.

According to an example embodiment, the sterilization device further comprises a chamber containing the cartridge therein.

According to an example embodiment, the sterilization device further comprises a vacuum pump connected to the chamber to decompress the chamber.

According to an example embodiment, the sterilization device further comprises a heating device heating the inside of the chamber.

According to an example embodiment, the sterilization device further comprises a packaging pouch coupled to one end of the cartridge and containing the article to be sterilized.

According to an example embodiment, the sterilization device further comprises a vacuum pump connected to the chamber and the sterilant provider to decompress the chamber, to decompress the inside of the packaging pouch through the injector, or to simultaneously decompress the chamber and inside of the packaging pouch through the injector.

Advantageous Effects of Disclosure

A cartridge and a sterilization device using the same according to the present disclosure are provided with a sterilant container for containing a sterilant and supply an appropriate amount of sterilant to a chamber or a packaging pouch, so that the sterilization device does not need a space for storing the sterilant, and thus the sterilization device may be miniaturized. In addition, since the cartridge and the sterilization device may supply the sterilant in a predetermined amount accurately, the sterilant may be prevented from remaining on the surface of the chamber or the packaging pouch after a sterilization process, thereby ensuring user safety.

A cartridge and a sterilization device using the same according to the present disclosure, by vaporizing a sterilant contained in a sterilant container inside the sterilization device, may reduce a distance from which the sterilant is supplied to a chamber or a packaging pouch, and thus a sterilization efficiency may be improved by not changing chemical properties of the sterilant at the time of sterilization.

A cartridge and a sterilization device using the same according to the present disclosure have a packaging pouch formed of a material which is not permeable to a sterilant and a material having high thermal conductivity to prevent condensation of the sterilant and maintain a uniform temperature inside the packaging pouch, thereby achieving a high sterilization efficiency.

A cartridge and a sterilization device using the same according to the present disclosure have a tag such as a bar code or a QR code for checking information about the cartridge on one side of the cartridge or on one side of a packaging pouch, and thus may check the use, authenticity, and aligned state of the cartridge. Accordingly, the sterilization reliability may be ensured by preventing reuse of the cartridge and the packaging pouch.

A cartridge and a sterilization device using the same according to the present disclosure are provided with a tray inside a packaging pouch, so that a sterilant may be diffused even if the outside of the packaging pouch is not decompressed, so that a small vacuum pump may be used, thereby miniaturizing the sterilization device.

BRIEF DESCRIPTION OF DRAWINGS

FIG. 1A is a plan view of a cartridge according to a first embodiment of the present disclosure.

FIGS. 3C and 3D are views for explaining a process of supplying a sterilant to the cartridge according to the second embodiment of the present disclosure and decompressing the inside of a packaging pouch.

FIG. 5A is a plan view of a cartridge according to a third embodiment of the present disclosure.

MODE OF DISCLOSURE

Figure 1B:
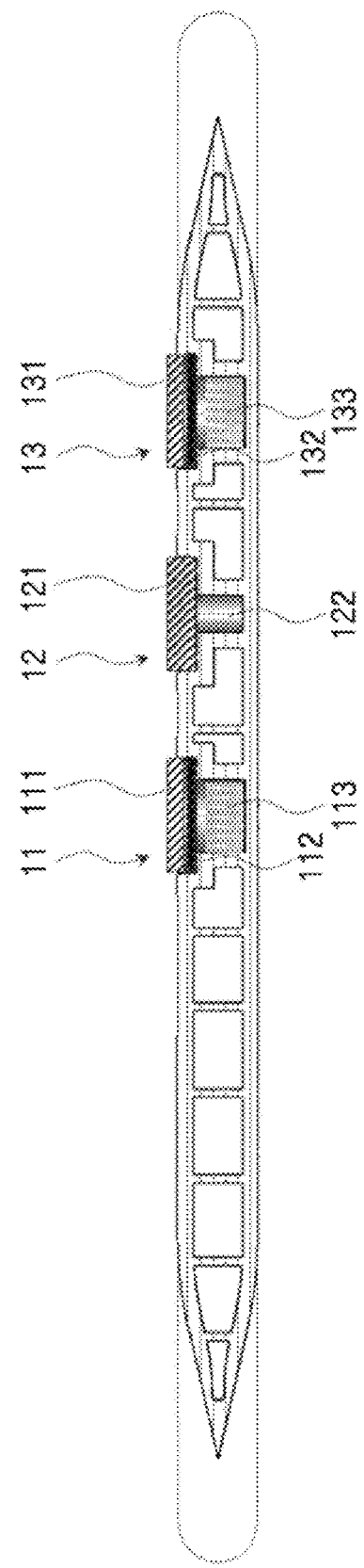
FIG. 1B is a cross-sectional view taken along dashed line A-A' of FIG. 1A.

Hereinafter, embodiments of the present disclosure will be described in detail with reference to the accompanying drawings. Technical problems, effects, and a method of achieving the same of the present disclosure may be more clearly understood with reference to the accompanying drawings and the description. However, the present disclosure is not limited to the embodiments described herein but may be embodied by other forms of embodiments that can be easily changed or employed by one of ordinary skill in the art.

Like reference numerals refer to like elements throughout. Accordingly, although the same reference numerals or like reference numerals are not mentioned or described in the drawings, they may be described with reference to other drawings.

Terms defined in the present specification should be interpreted according to the definition of the specification regardless of the general usage of the term, and terms not defined should be interpreted according to the meaning recognized by one of ordinary skill in the art and the dictionary meaning.

A cartridge according to a first embodiment of the present disclosure will be described with reference to FIGS. 1A to 2. FIG. 1A is a plan view of a cartridge according to a first embodiment of the present disclosure, and FIG. 1B is a cross-sectional view taken along dashed line A-A' of FIG. 1A. A cartridge 10 according to the first embodiment of the present disclosure includes a sterilant container 11, an injector 12, an auxiliary sterilant container 13, a coupling portion 14, a tag 15, and a body portion 16.

The sterilant container 11 has a certain inner space to contain or store a sterilant 113 used for sterilization, and contains the sterilant 113 such as hydrogen peroxide therein. The sterilant container 11 is sealed with an elastic sealing material 111 having elasticity so that the sterilant 113 contained in the sterilant container 11 does not flow out. The elastic sealing material 111 may be penetrated by a sharp object such as a needle 841 (in FIG. 9), and needs to be elastic enough to return to the sealed state by closing the penetrated portion by its elasticity after the needle is removed. The elastic sealing material 111 may be made using silicon, rubber, a synthetic resin, and the like having the above elasticity. A film 112 may be further included between the sterilant container 11 and the elastic sealing material 111 to more reliably prevent the outflow of the sterilant. The film 112 is formed of a material that may be penetrated by a sharp object such as a needle without a chemical reaction with the sterilant.

The auxiliary sterilant container 13 has the same structure as the sterilant container 11. The auxiliary sterilant container 13 is to supply an additional sterilant 133 when the sterilization device needs to perform a sterilization process twice, and may not be included when the sterilization process is performed only once.

The injector 12 is used to supply the sterilant 113 to a chamber 970 (of FIG. 10) or a packaging pouch 27 (of FIG. 3A) or 37 (of FIG. 5A) coupled to the cartridge 10 or to decompress the inside of the packaging pouch. In order to achieve this function, the injector 12 is formed with a path 122 connected to the chamber of the sterilization device or the packaging pouch. The sterilant 113 is injected into the chamber of the sterilization device or the packaging pouch through the path 122, or gas inside the packaging pouch is exhausted to decompress the inside of the packaging pouch. The injector 12 may be penetrated by a sharp object such as a needle 831 (in FIG. 9), and after the needle is removed, is sealed with an elastic sealing material 121 having elasticity enough to return to the sealed state by closing the penetrated portion by its elasticity. Unlike the sterilant container 11, the injector 12 does not contain the sterilant 113 inside, and thus, the sealed state after the needle is removed may be different from a sealed state required for the sterilant container 11. Accordingly, the elastic sealing material 121 of the injector 12 may be formed of a material having an elastic force different from that of the elastic sealing material 111 of the sterilant container 11. For example, silicon with a lower elastic force may be used.

The coupling portion 14 is for coupling the cartridge 10 to a sterilization device 800 (of FIG. 7) or 900 (of FIG. 10), and a specific shape thereof may vary according to the structure of the sterilization device. For example, the coupling portion 14 is formed protruding or recessed than the body portion 16 or integrally formed with the body portion 16 so that the cartridge 10 may be located or fixed in a certain position of the sterilization device.

The tag 15 refers to a mark such as a bar code, a QR code, etc., which may check information about the cartridge 10, and is formed on one surface of the cartridge 10 so that the sterilization device may check it. A specific image or character of the tag 15 may be formed according to a known method of generating a code, such as a conventional bar code or QR code.

The body portion 16 is to provide a space in which the sterilant container 11, the injector 12, and the coupling portion 14, etc. may be coupled or located, and a specific shape thereof may vary according to the structure or shape of the sterilization device.

Figure 2:
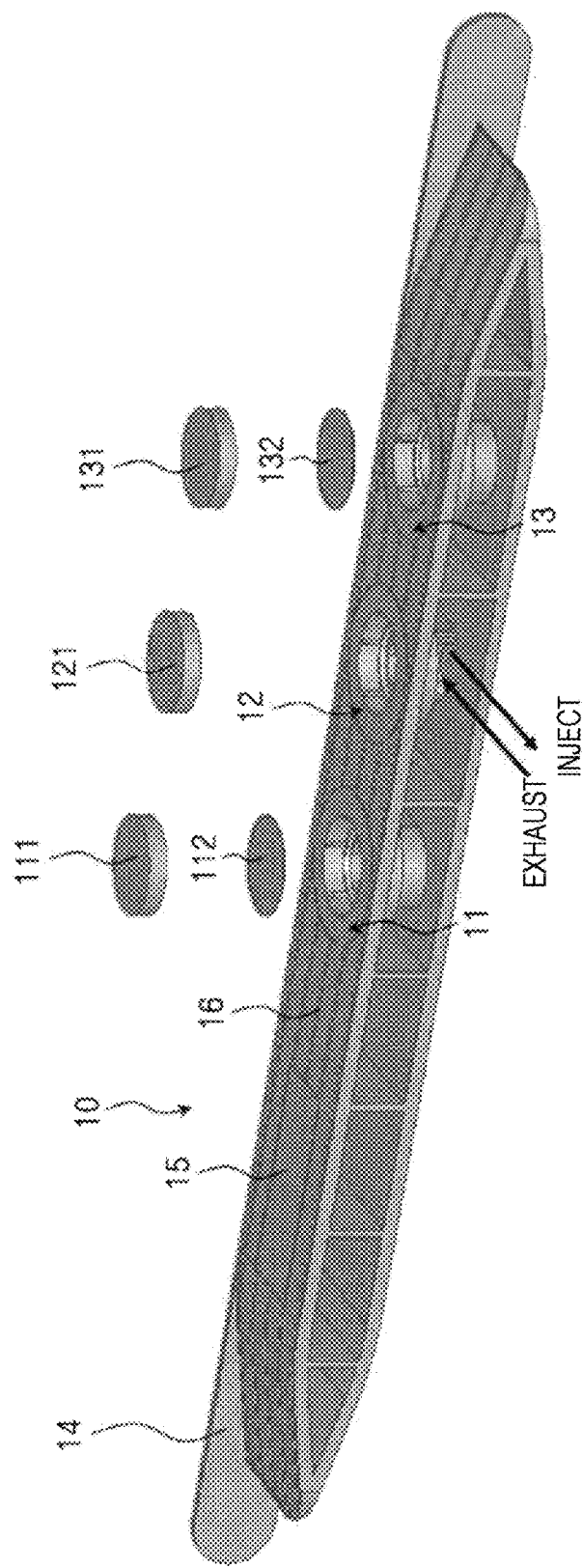
FIG. 2 is a perspective view of a cartridge according to the first embodiment of the present disclosure.

FIG. 2 is a perspective view of a cartridge according to the first embodiment of the present disclosure. In FIG. 2, the elastic sealing material 111 of the sterilant container 11 and the elastic sealing material 121 of the injector 12 are separately shown in order to explain a coupling method thereof in more detail. The sterilant 113 is supplied to the inside of the packaging pouch and the chamber of the sterilization device in a direction A shown in FIG. 2, and gas inside the packaging pouch is exhausted in a direction B to decompress the inside of the packaging pouch.

A cartridge according to a second embodiment of the present disclosure will be described with reference to FIGS. 3A to 4. Since the cartridge according to the second embodiment of the present disclosure is made by further modifying a portion of the configuration of the cartridge according to the first embodiment of the present disclosure, the detailed description of the configuration substantially the same as or similar to the configuration of the cartridge according to the first embodiment of the present disclosure among the configuration of the cartridge according to the second embodiment of the present disclosure will not be given herein.

Figure 3A:
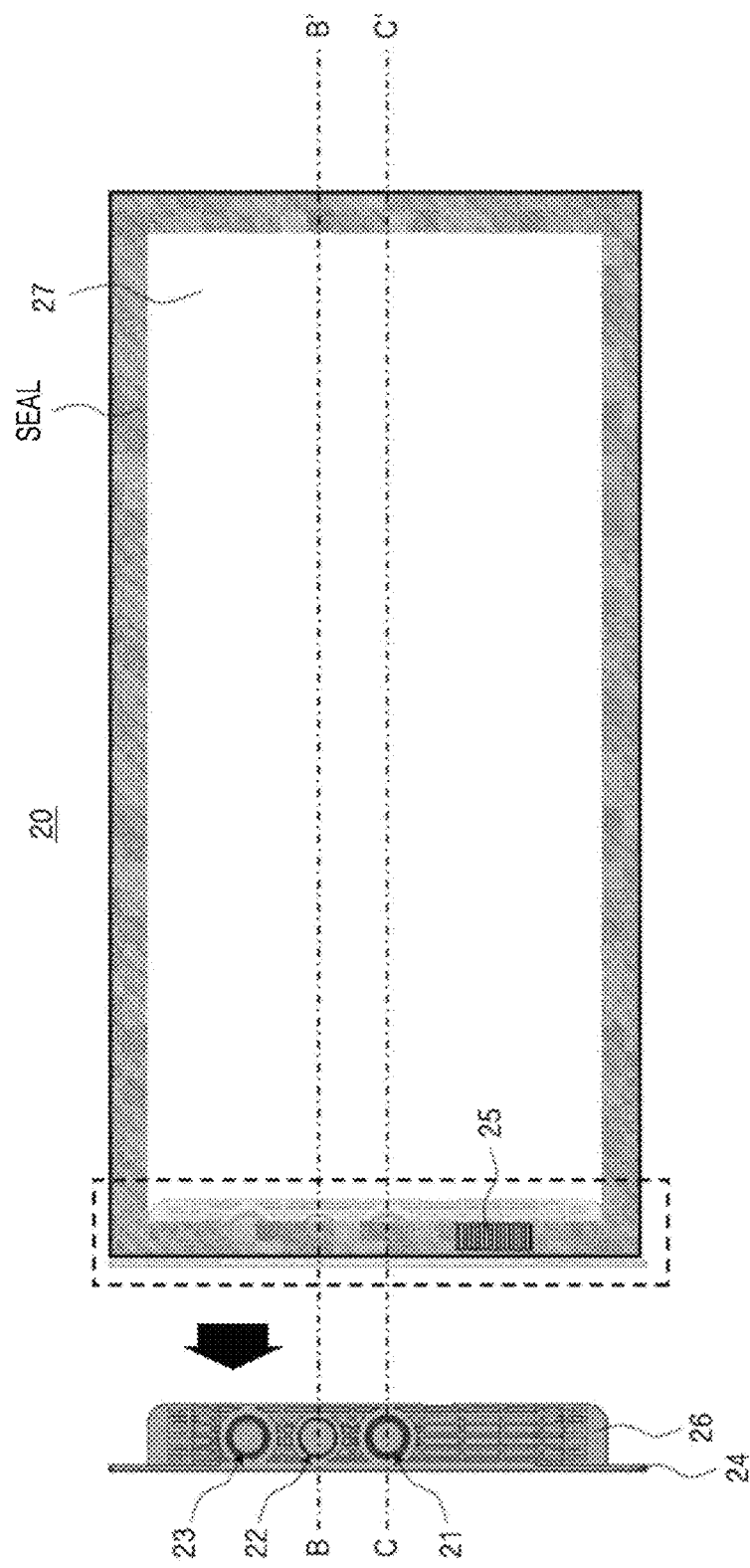
FIG. 3A is a plan view of a cartridge according to a second embodiment of the present disclosure.

FIG. 3A is a plan view of the cartridge according to the second embodiment of the present disclosure. A cartridge 20 according to the second embodiment of the present disclosure includes a sterilant container 21, an injector 22, an auxiliary sterilant container 23, a coupling portion 24, a tag 25, a body portion 26, and the packaging pouch 27. The cartridge 20 according to the second embodiment of the present disclosure is further provided with the packaging pouch 27 in the cartridge 10 according to the first embodiment of the present disclosure, and the packaging pouch 27 is hermetically coupled to the body portion 26 of the cartridge 20. Since an article to be sterilized needs to be contained in the packaging pouch 27, at least one side of the packaging pouch 27 is open before sterilization, but all sides of the packaging pouch 27 needs to be sealed after containing the article to be sterilized and before performing sterilization. As shown by the diagonal line in FIG. 3A (a portion indicated by "sealing"), an edge portion of the packaging pouch 27 may be sealed by thermocompression bonding. In the case of a cartridge having a packaging pouch as in the second embodiment of the present disclosure, the tag 25 may be formed on the body portion 26 of the cartridge 20 or one surface of the packaging pouch 27.

Figure 3B:
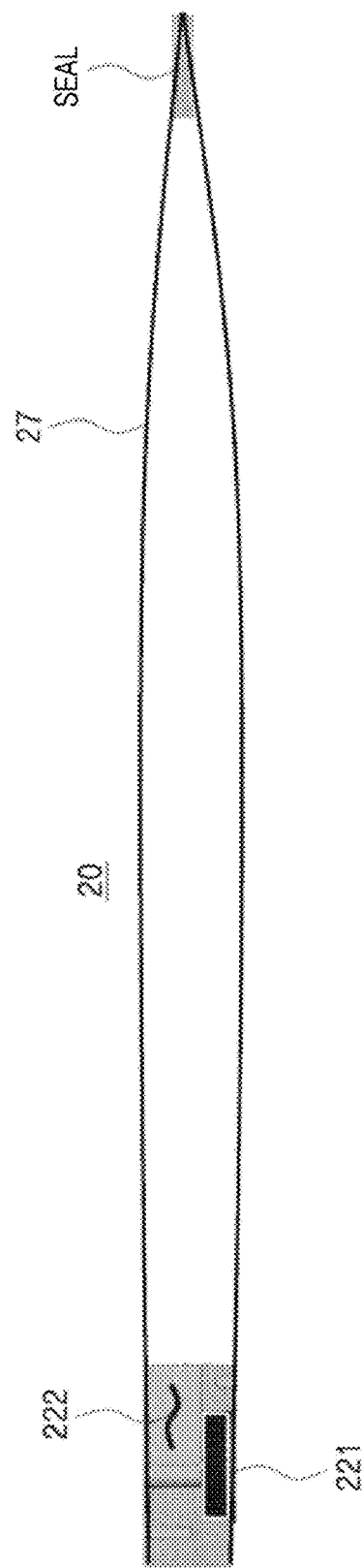
FIG. 3B is a cross-sectional view taken along line B-B' of FIG. 3A.

FIG. 3B is a cross-sectional view taken along line B-B' of FIG. 3A. In FIG. 3B, cross sections of the injector 22 and the packaging pouch 27 may be checked. As described above, a path 222 is formed in the injector 22, and an elastic sealing material 221 seals the path 222.

FIGS. 3C and 3D are views for explaining a sterilant supply and exhaust process through the injector 22. The sterilant supply process into the packaging pouch 27 shown in FIG. 3C includes (i) positioning the needle 831 (in FIG. 9) in or near the path 222 formed in the injector 22 by penetrating the elastic sealing material 221 using a sharp object such as the needle 831 and (ii) injecting the sterilant received from the needle into the package 27 through the path 222. Decompressing the inside of the packaging pouch 27 shown in FIG. 3C includes (i) placing the needle into or near the path 222 formed in the injector 22 by penetrating the elastic sealing material 221 using the needle and (ii) exhausting gas inside the packaging pouch 27 through the needle and the path 222 formed in the injector 22.

Figure 3E:
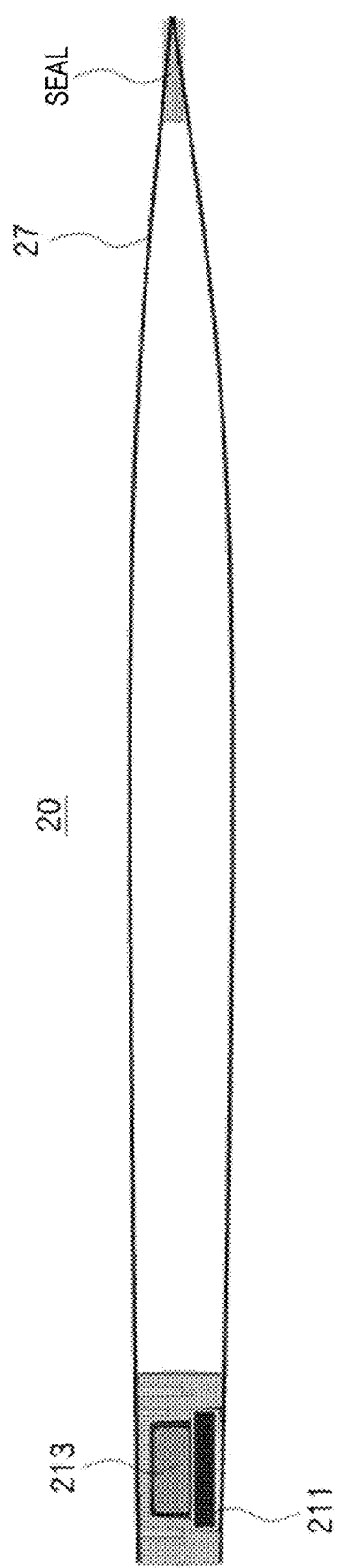
FIG. 3E is a cross-sectional view taken along dashed line C-C' of FIG. 4A.

FIG. 3E is a cross-sectional view taken along dashed line C-C' of FIG. 3A. In FIG. 3E, cross sections of the injector 22 and the packaging pouch 27 may be checked. As described above, the sterilant container 21 contains a sterilant 213 and seals the sterilant container 21 so that the elastic sealing material 211 does not leak out of the sterilant 213.

Figure 3F:
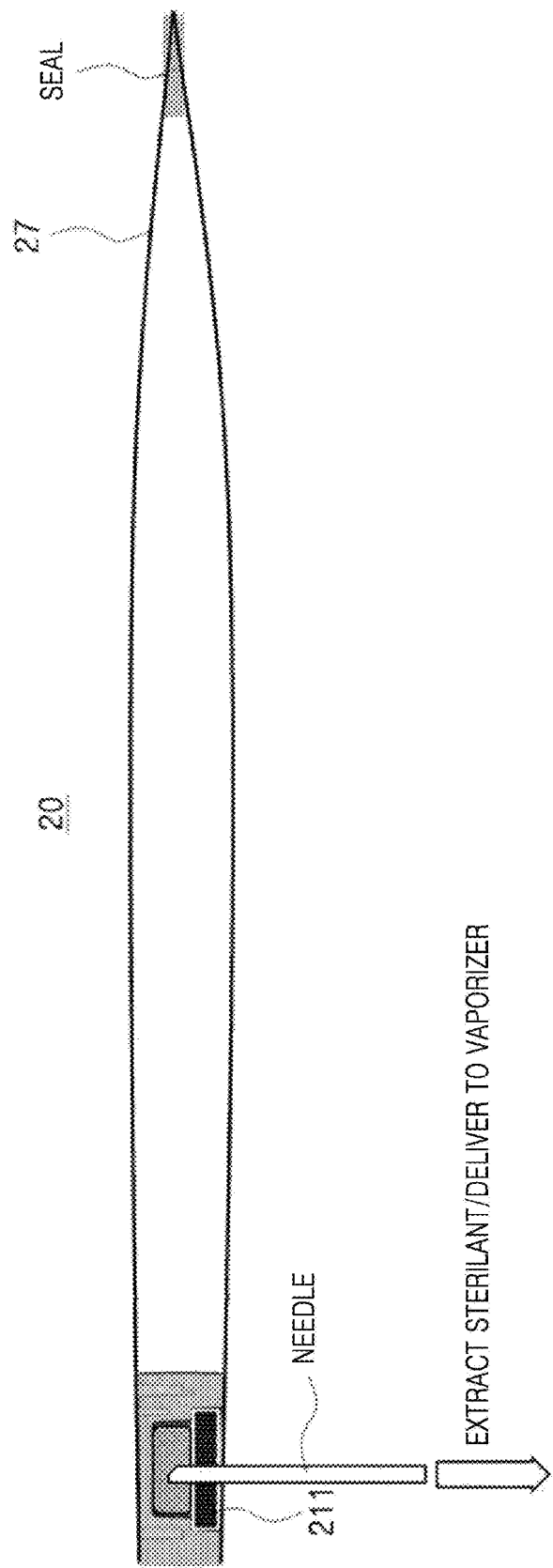
FIG. 3F is a view for explaining a process of extracting a sterilant from a sterilant container of the cartridge according to the second embodiment of the present disclosure.
Figure 9:
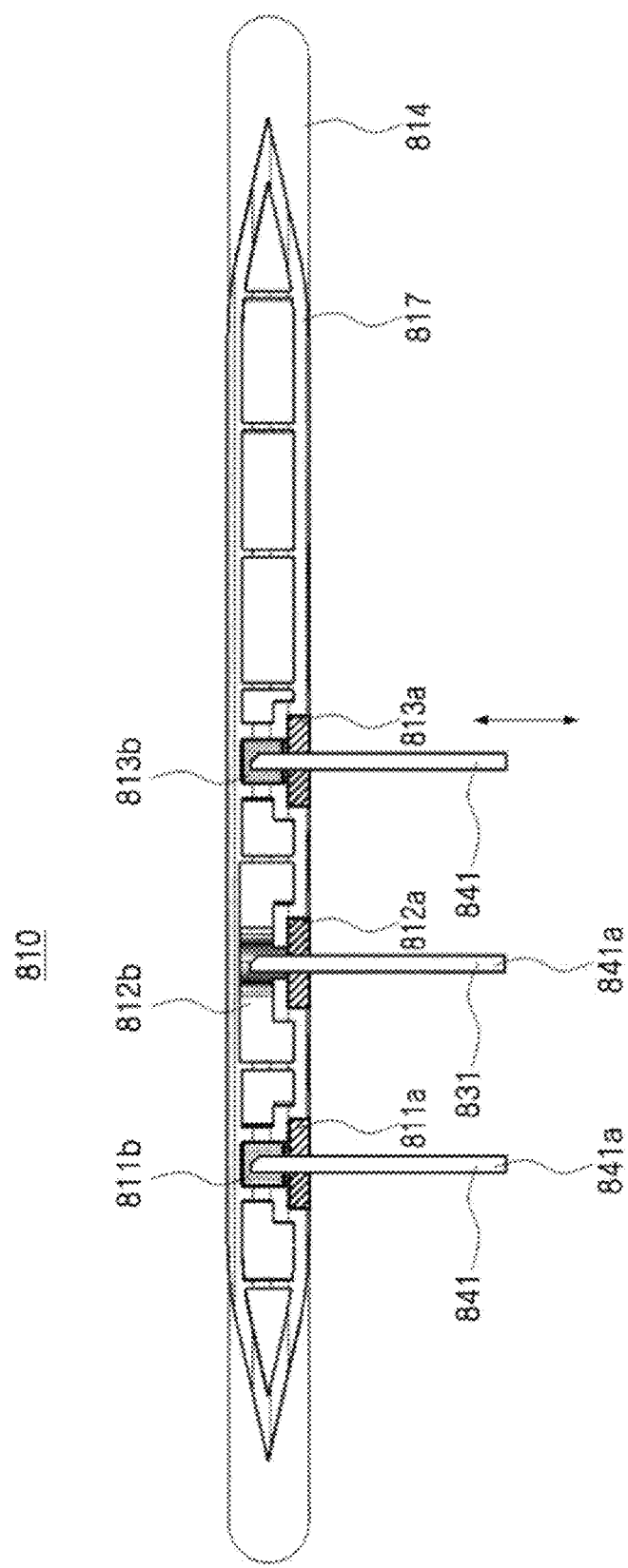
FIG. 9 is a view for explaining a process in which the sterilization device according to the fifth embodiment of the present disclosure extracts a sterilant from a sterilant container and supplies the sterilant to a packaging pouch through a cartridge according to the fifth embodiment of the present disclosure.
Figure 10:
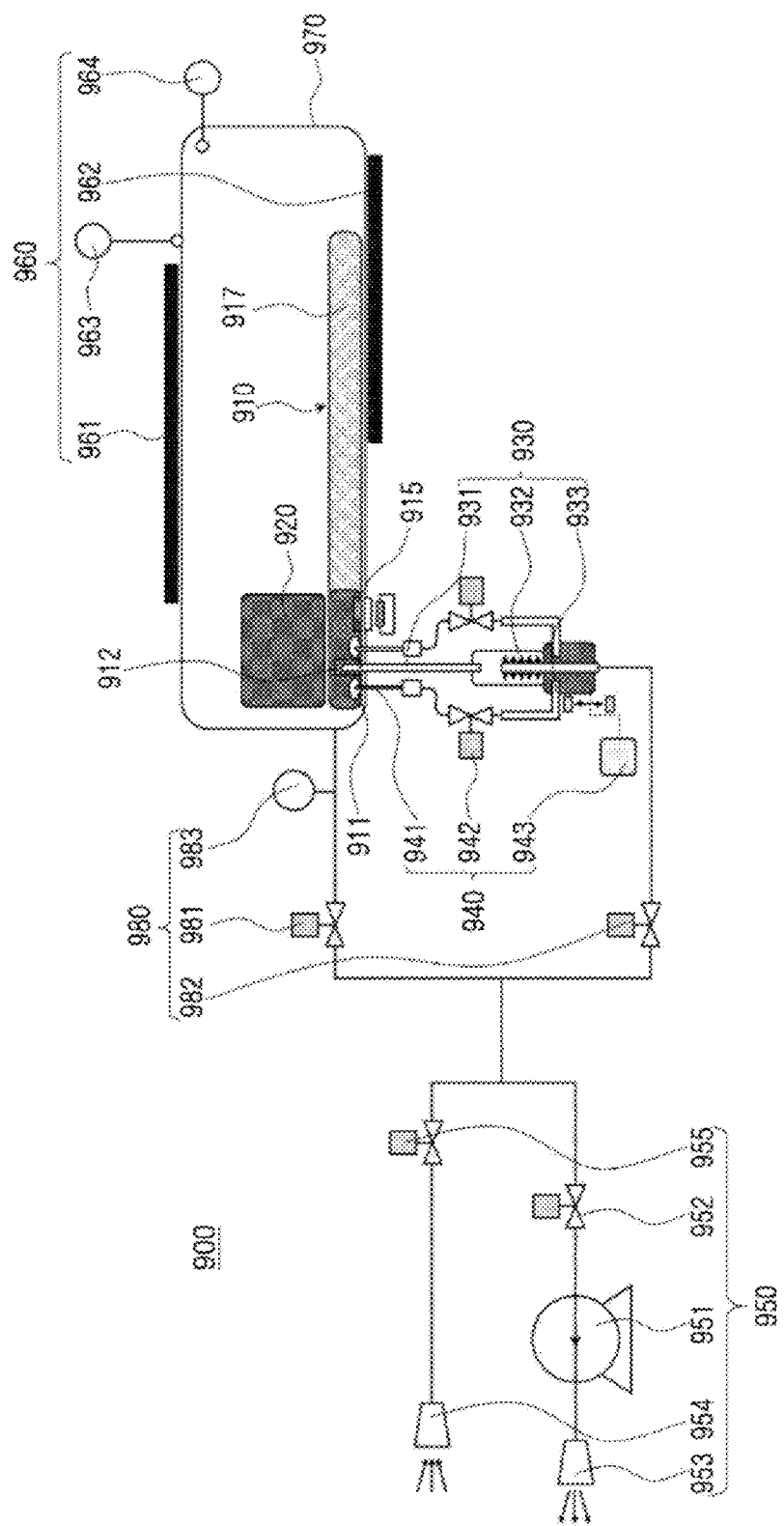
FIG. 10 is a conceptual diagram of a sterilization device according to a sixth embodiment of the present disclosure.

FIG. 3F is a view for explaining a process of extracting the sterilant 213 contained in the sterilant container 21 to a sterilant 800 (of FIG. 7) or 900 (of FIG. 10). The process of extracting the sterilant 213 shown in FIG. 3F includes (i) positioning the needle 841 (in FIG. 9) in the sterilant 213 contained in the sterilant container 21 by penetrating the elastic sealing material 221 using a sharp object such as the needle 841 and (ii) extracting the sterilant 213 into the sterilization device 800 (of FIG. 7) or 900 (of FIG. 10) through the needle.

Figure 4:
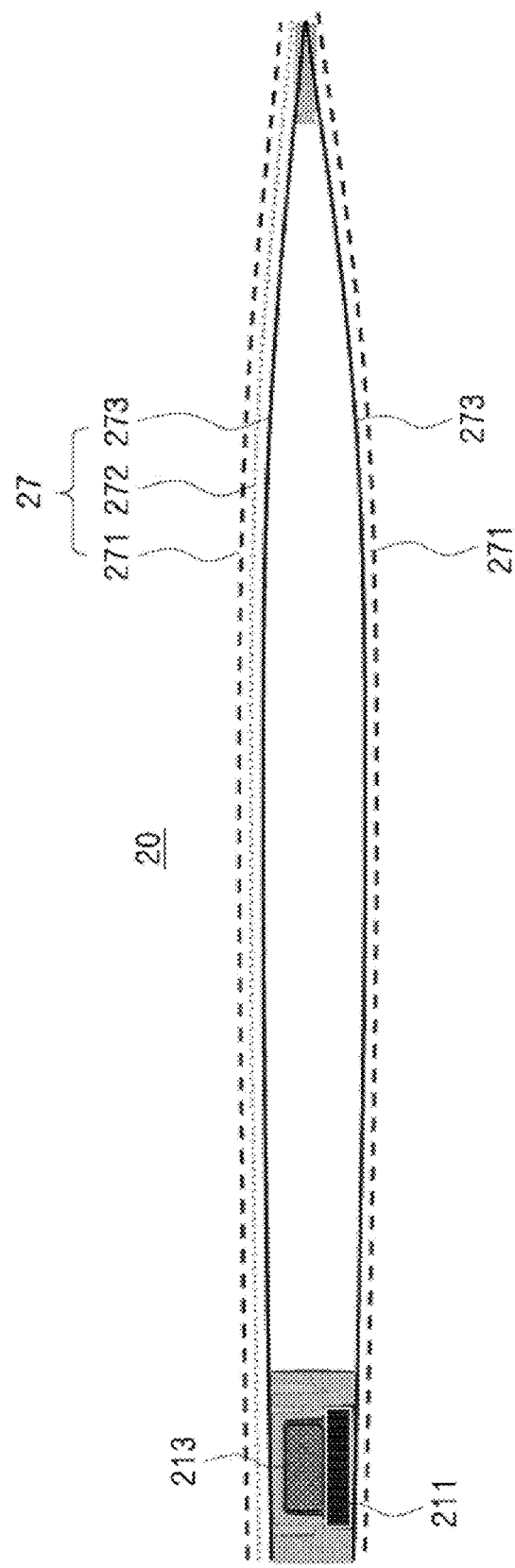
FIG. 4 is a cross-sectional view of a packaging pouch according to the second embodiment of the present disclosure.

FIG. 4 is a cross-sectional view for explaining a specific configuration of the packaging pouch 27 applied to the cartridge 20 according to the second embodiment of the present disclosure. The packaging pouch 27 is composed of a layer of an impermeable film 271 and a heat-adhesive film 273, wherein one surface of the packaging pouch 27 is further provided with a heat conductive film 272 between the impermeable film 271 and the heat-adhesive film 273, and a surface of the packaging pouch 27 not provided with the heat conductive film 272 is formed to be transparent. The impermeable film 271 refers to a film that does not permeate gas or liquid to maintain airtightness, and may be formed using, for example, a nylon resin. The heat-adhesive film 273 refers to a film that is fused when heat of a specific temperature or more is applied thereto. For example, the heat-adhesive film 273 may be formed using a polypropylene (PP) resin and a polyethylene (PE) resin. The heat conductive film 272 refers to a film having higher thermal conductivity than the impermeable film 271 and the heat-adhesive adhesive film 273, and may be formed using, for example, an aluminum film or an aluminum coating film among metallic films.

A cartridge according to a third embodiment of the present disclosure will be described with reference to FIGS. 5A to 6. Since the cartridge according to the third embodiment of the present disclosure is made by further modifying a portion of the configuration of the cartridge according to the first embodiment of the present disclosure, the detailed description of the configuration substantially the same as or similar to the configuration of the cartridge according to the first embodiment of the present disclosure among the configuration of the cartridge according to the third embodiment of the present disclosure will not be given herein.

FIG. 5A is a plan view of a cartridge according to the third embodiment of the present disclosure. A cartridge 30 according to the third embodiment of the present disclosure includes a sterilant container 31, an injector 32, an auxiliary sterilant container 33, a coupling portion 34, a tag 35, a body portion 36, the packaging pouch 37, and a tray 38.

The cartridge 30 according to the third embodiment of the present disclosure further includes the packing material 37 and the tray 38 in the cartridge 10 according to the first embodiment of the present disclosure. The packaging pouch 37 is hermetically coupled to the body portion 36 of the cartridge 30, and the tray 38 is in the packaging pouch 37. Since an article to be sterilized needs to be contained in the packaging pouch 27 and the tray 38, at least one side of the packaging pouch 27 is open before sterilization, but all surfaces of the packaging pouch 27 needs to be sealed after containing the article to be sterilized and before performing sterilization. As shown by the diagonal line in FIG. 5A (a portion indicated by "sealing"), an edge portion of the packaging pouch 37 may be sealed by thermocompression bonding. In the case of a cartridge having a packaging pouch as in the third embodiment of the present disclosure, the tag 35 may be formed on the body portion 36 of the cartridge 30 or one surface of the packaging pouch 37.

Figure 5B:
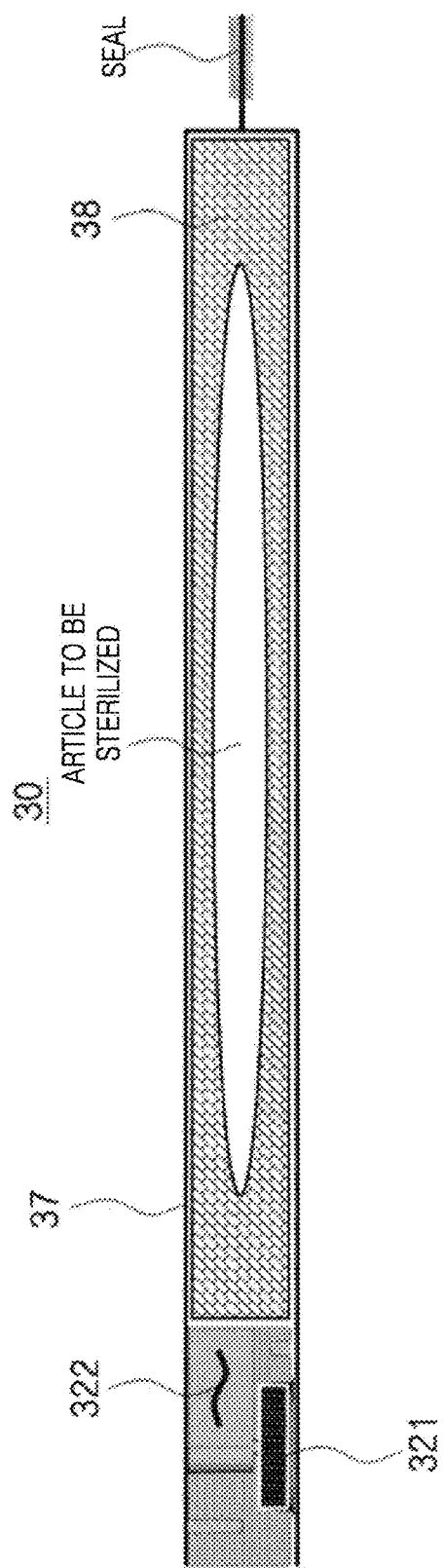
FIG. 5B is a cross-sectional view taken along line D-D' of FIG. 5A.

FIG. 5B is a cross-sectional view taken along line D-D' of FIG. 5A. In FIG. 5B, cross sections of the injector 32, the tray 38, and the packaging pouch 37 may be checked. As described above, a path 322 is formed in the injector 32, and an elastic sealing material 321 seals the path 322.

Figure 5C:
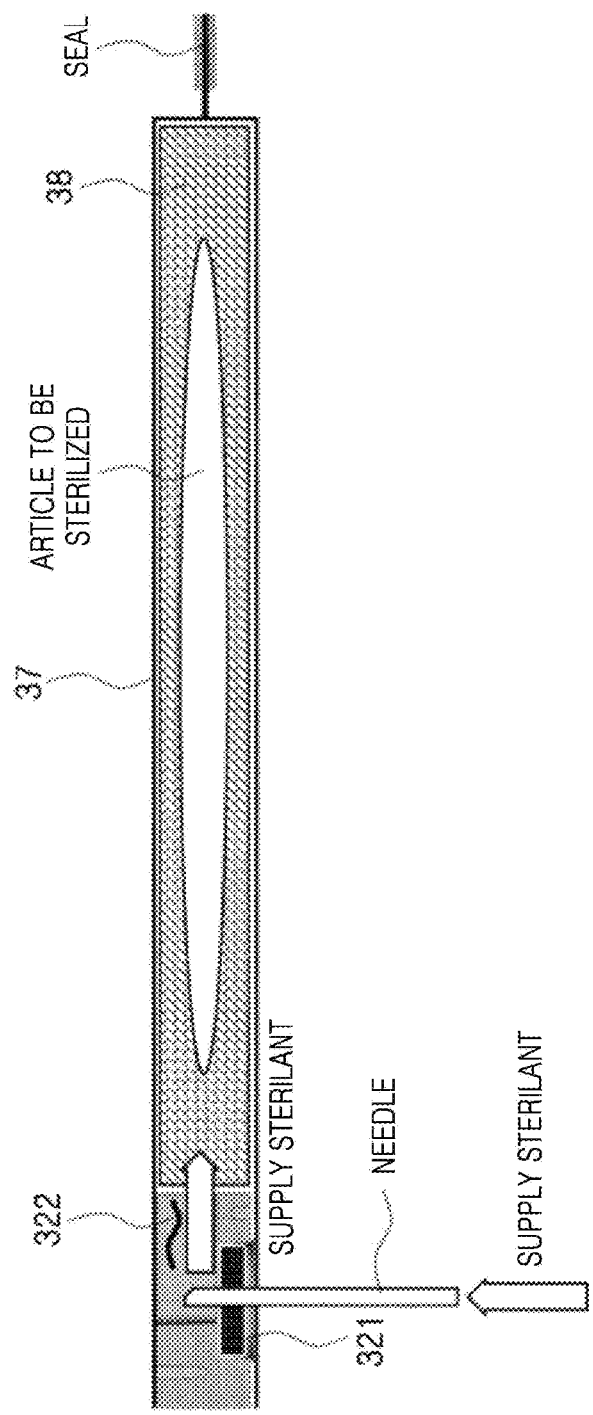
FIGS. 5C and 5D are views for explaining a process of supplying a sterilant to the cartridge according to the third embodiment of the present disclosure and decompressing the inside of a packaging pouch.
Figure 5D:
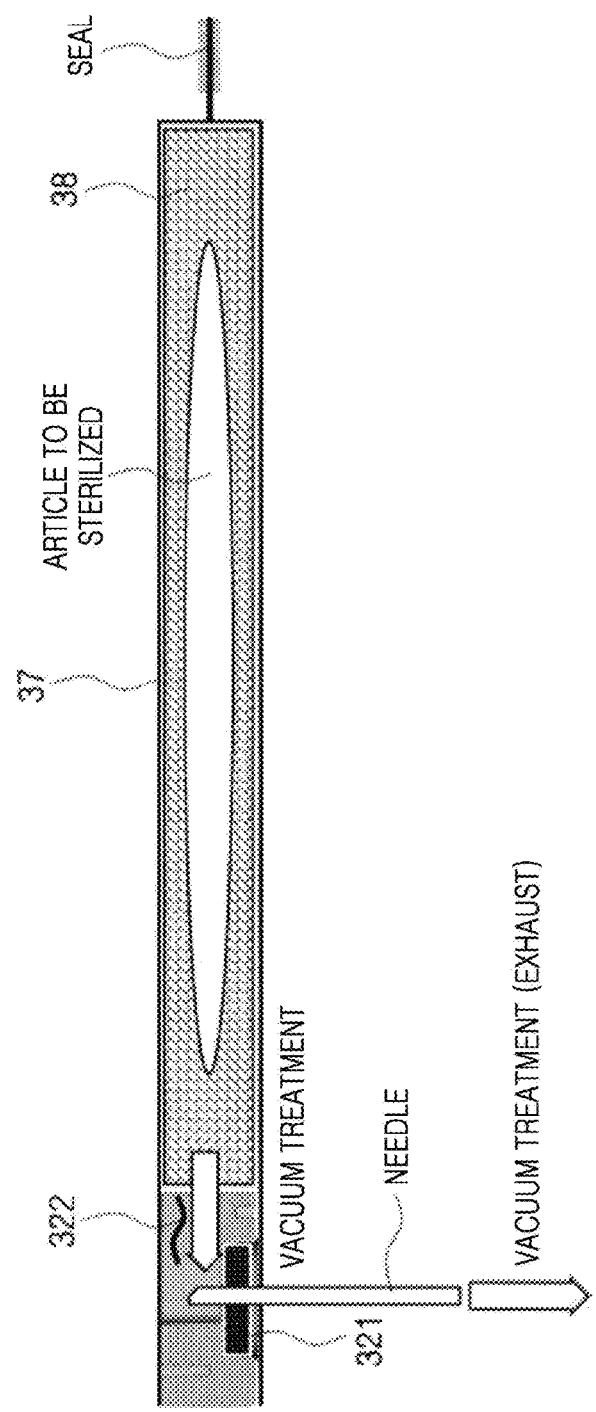

FIGS. 5C and 5D are views for explaining a sterilant supply and exhaust process through the injector 32. The sterilant supply process into the packaging pouch 37 shown in FIG. 5C includes (i) positioning the needle 831 (in FIG. 9) in or near the path 322 formed in the injector 32 by penetrating the elastic sealing material 321 using a sharp object such as the needle 831 and (ii) injecting the sterilant received from the needle into the package 37 through the path 322. Decompressing the inside of the packaging pouch 37 shown in FIG. 5D includes (i) placing the needle into or near the path 322 formed in the injector 32 by penetrating the elastic sealing material 321 using the needle and (ii) exhausting the gas inside the packaging pouch 37 through the needle and the path 322 formed in the injector 32.

In the case of the cartridge 30 according to the third embodiment of the present disclosure, since the tray 38 is present to secure a space between the article to be sterilized and the packaging pouch 37 in the sterilant supply and exhaust process, the vaporized sterilant may be smoothly delivered to the article to be sterilized, and the article to be sterilized may be prevented from being pressed due to a pressure difference between the inside and the outside of the packing material 37 even after the exhaust process.

Figure 6:
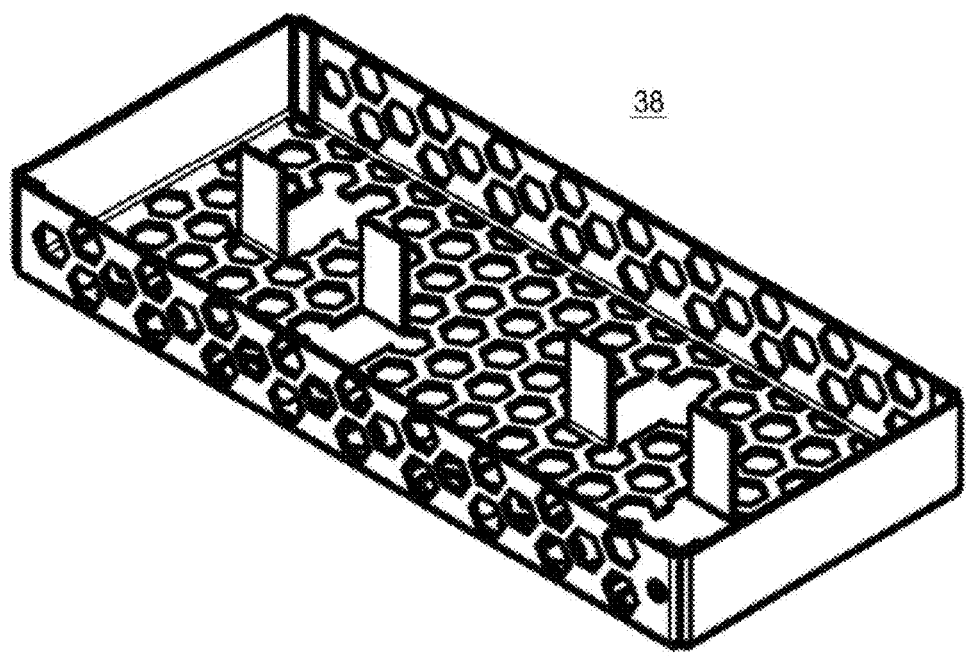
FIG. 6 is a perspective view of a tray according to the third embodiment of the present disclosure.

FIG. 6 is a perspective view of the tray 38. The tray 38 is a structure for supporting the packaging pouch 37 to secure a space in which the sterilant may be diffused or moved and to prevent the article to be sterilized from being pressed (e.g., a cuboid shape with ventilation holes), and a specific shape thereof is not limited thereto.

The cartridge according to the fourth embodiment of the present disclosure excludes the tag 25 from the cartridge according to the second embodiment of the present disclosure. The cartridge according to the fourth embodiment of the present disclosure includes a sterilant container for storing a sterilant used for sterilization, an injector for receiving the sterilant contained in the sterilant container through the sterilization device to deliver to an article to be sterilized, a coupling portion coupled to the sterilization device to guide the cartridge to be aligned at a certain position, and a packaging pouch containing the article to be sterilized, wherein the packing material is formed of a film that does not permeate liquid or gas, and one end of the packing material is coupled to the cartridge to maintain a sealed state.

Figure 7:
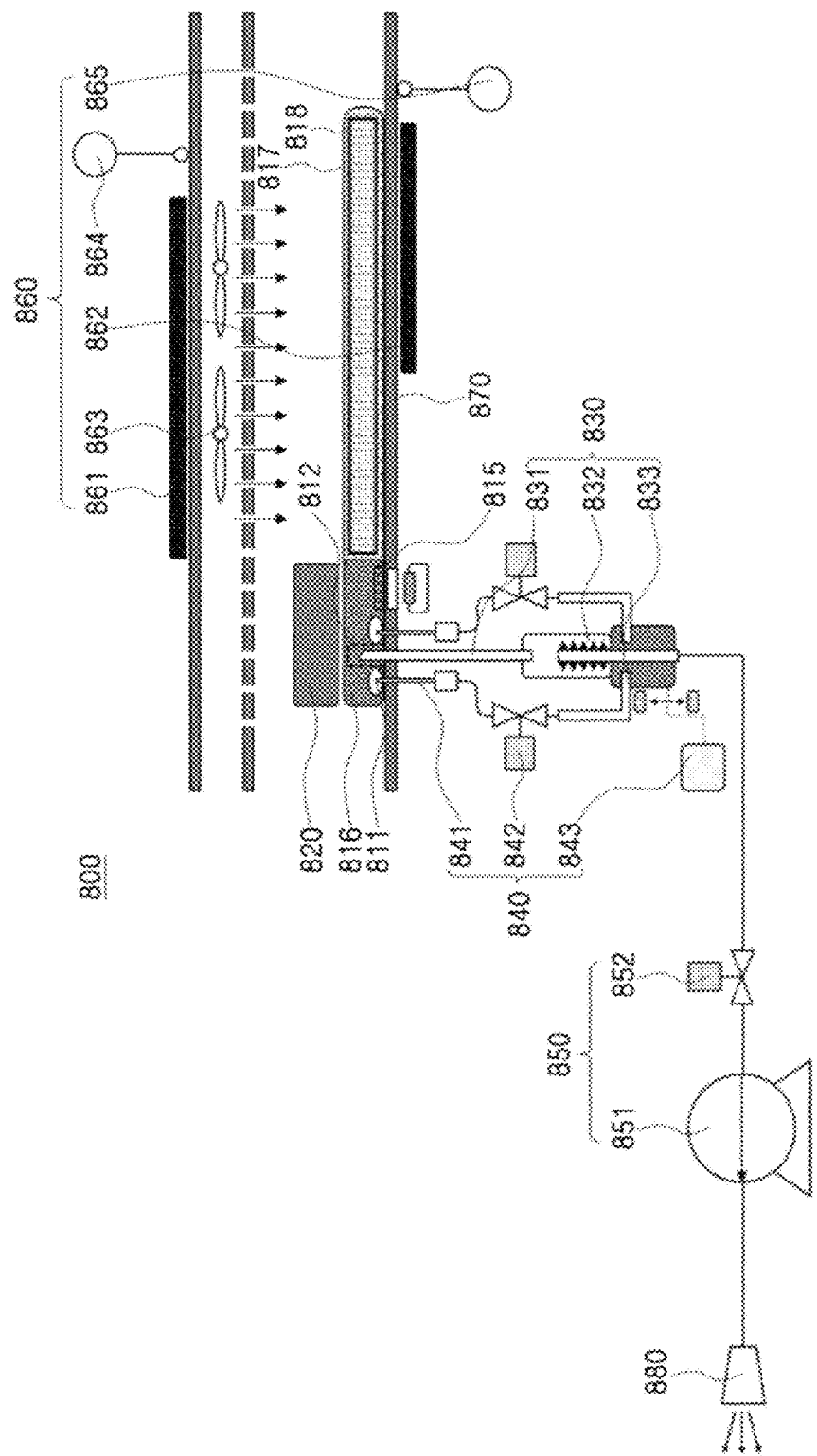
FIG. 7 is a conceptual diagram of a sterilization device according to a fifth embodiment of the present disclosure.
Figure 8A:
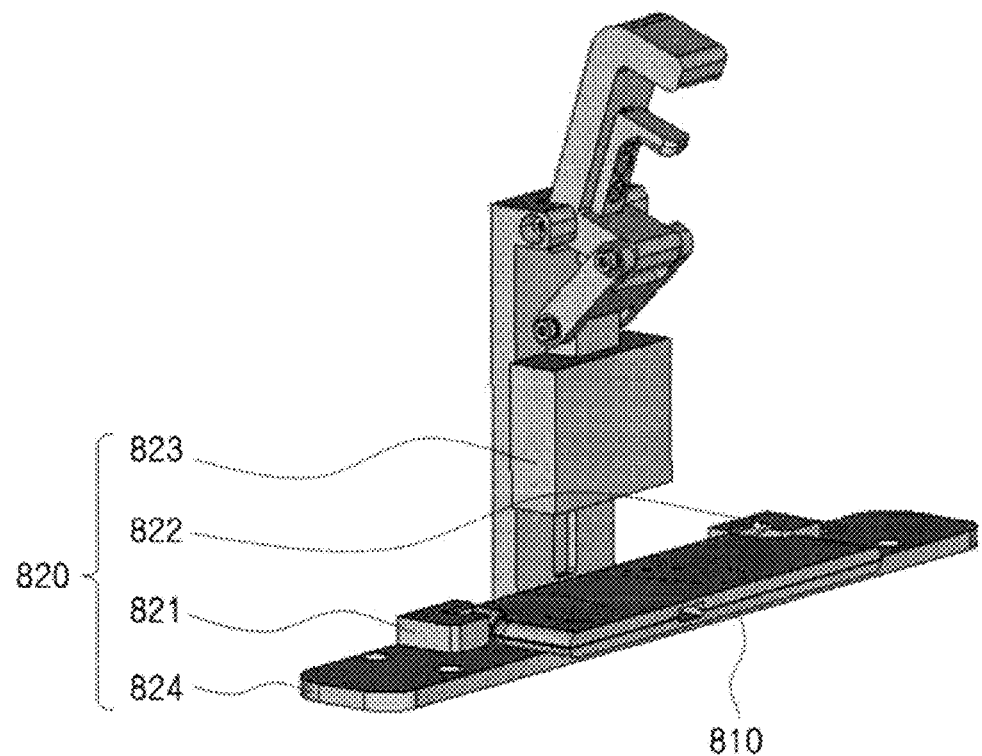
FIG. 8A is a perspective view of a shape in which a coupling portion is contained in a coupling container according to the fifth embodiment of the present disclosure.
Figure 8B:
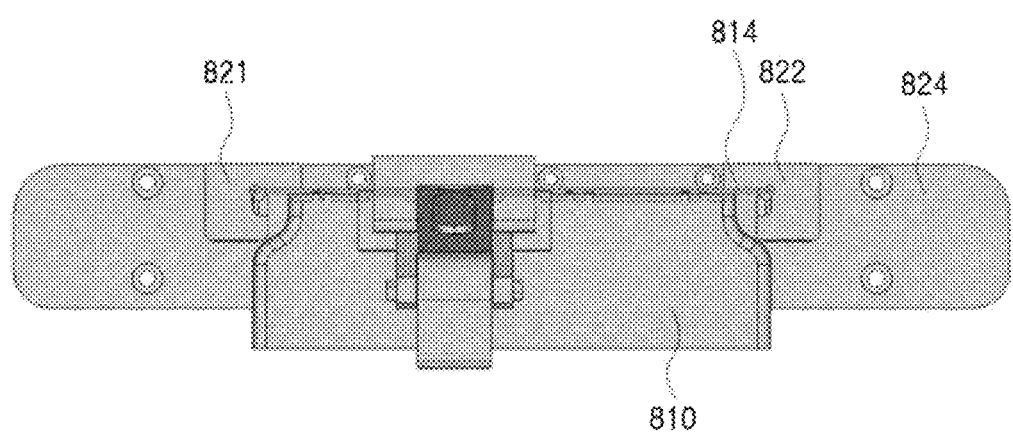
FIG. 8B is a plan view of a shape in which the coupling portion is contained in the coupling container according to the fifth embodiment of the present disclosure.

A sterilization device 800 according to a fifth embodiment of the present disclosure will be described with reference to FIGS. 7 to 9. FIG. 7 is a conceptual diagram of the sterilization device 800 according to the fifth embodiment of the present disclosure. The sterilization device 800 according to the fifth embodiment of the present disclosure includes a cartridge 810, a coupling container 820, a sterilant provider 830, a sterilant extractor 840, a vacuum pump module 850, a heating module 86, a device body 870, and a filter 880.

The cartridge 810 includes a sterilant container 811, an injector 812, an auxiliary sterilant container 813, a coupling portion 814 (of FIG. 8), a tag 815, a body portion 816, a packaging pouch 817, and a tray 818. Since the cartridge 810 is substantially the same as the cartridge 30 according to the third embodiment of the present disclosure, a detailed description of each component constituting the cartridge 810 will not be given herein.

The coupling container 820, which is configured to contain the cartridge 810 such that the cartridge 810 is located at a certain place, is fixed to the device body 870 and coupled to the coupling portion 814 (of FIG. 8) of the cartridge 810.

The sterilant provider 830 may include a needle 831 which may penetrate an elastic sealing material (not shown) that seals the injector 812 of the cartridge 810, a vaporizer 832 formed around the needle 831, and a pipe 833 receiving a sterilant extracted from the sterilant extractor 840.

The sterilant extractor 840 includes a needle 841 which may penetrate an elastic sealing material (not shown) that seals the sterilant container 811 of the cartridge 810, a first valve 842 for controlling a sterilant flow, and a driver 843 for moving the needle 841 in a vertical direction.

The vacuum pump module 850 includes a vacuum pump 851 and a second valve 852 for controlling the flow of gas.

The heating module 860 includes heaters 861 and 862, a fan 863, and temperature measuring devices 864 and 865. The heaters 861 and 862 are attached to upper and lower surfaces of the device body 870 to heat the inside of the device body 870, the fan 863 circulates the heated internal gas to improve the heating rate and makes the internal temperature of the device body 870 uniform. The temperature measuring devices 864 and 865 measure the temperature of the device body 870 or the inside thereof so that the device body 870 or the inside thereof may be maintained at a certain temperature.

The device body 870 is a structure for supporting or containing the cartridge 810 and the coupling container 820, and a specific shape thereof is not limited thereto. The device body 870 may be sealed or opened.

The filter 880, when exhausting gas received from the vacuum pump 851 in a process of decompressing the inside of the packaging pouch 817 to the outside, is connected to the vacuum pump module 850 to exhaust harmful components included in the gas.

A detailed structure and an operation method of the coupling container 820 applied to the sterilization device 800 according to the fifth embodiment of the present disclosure will be described with reference to FIGS. 8A and 8B. FIG. 8A is a perspective view of the coupling container 820 applicable to the sterilization device 800 and the cartridge 810 (the packaging pouch and the tray are not shown) according to the present disclosure coupled thereto, and FIG. 8B is a plan view of FIG. 8A.

The coupling container 820 includes loading/unloading portions 821 and 822, a fixing portion 823, and a support portion 824. Here, the loading/unloading portions 821 and 822 have a structure corresponding to the coupling portion 814 of the cartridge 810, and are directly coupled to the coupling portion 814. Also, the fixing unit 823 presses and fixes the cartridge 810 from above to maintain the cartridge 810 in a coupled state (However, as long as it is a device for fixing, the specific structure and method of the fixing are not limited thereto). The loading/unloading portions 821 and 822 and the fixing portion 823 are installed and supported by the support portion 824, and the support portion 824 is coupled to the device body 870 to allow the coupling container 820 to be located in the device body 870. However, the support portion 824 may be formed as a portion of the device body 870 rather than a separate component or configuration.

An operation method of the sterilization device 800 according to a fifth embodiment of the present disclosure will be described with reference to FIGS. 7 to 9. FIG. 9 is a cross-sectional view of a sterilant extracting, injecting, and exhausting process of the sterilization device 800 according to the fifth embodiment of the present disclosure, wherein the needles 831 and 841 are inserted into the cartridge 810.

The sterilization device 800 according to the fifth embodiment of the present disclosure includes:

(a) containing an article to be sterilized in the packaging pouch 817 of the cartridge 810 and coupling the cartridge 810 to the coupling container 820 of the sterilization device 800, wherein information about the tag 815 of the cartridge 810 is reviewed to determine whether the cartridge 810 is genuine or reused;

(b) moving the needle 841 of the sterilant extractor 840 and the needle 831 of the sterilant provider 830 in a direction of the cartridge 810 by the driver 843 provided in the sterilant extractor 840 such that the needles 831 and 841 penetrate the elastic sealants 811a and 812a sealing the sterilant container 811 and the injector 812 of the cartridge 810, respectively, wherein the needle 831 of the sterilant provider 830 may be moved separately by a separate driving device;

(c) exhausting gas in the packaging pouch 817 to reduce the pressure through a path 812b formed in an inner tube 831a of the needle 831 of the sterilant provider 830 and the injector 812 of the cartridge 810 by the sterilant provider 830, which is connected to the vacuum pump module 850, according to operations of the vacuum pump 851, the first valve 842, and the second valve 852 (closing of the first valve, opening of the second valve);

(d) operating the heating module 860 to adjust the temperature inside the device body 870 to a set temperature, wherein the temperature control may be performed after operation (a), before operation (d), or simultaneously with other operations;

(e) extracting a sterilant 811b using a pressure difference through an inner tube 841a formed in the needle 841 of the sterilant extractor 840 by the sterilant extractor 840, which is connected to the vacuum pump module 850, according to operations of the vacuum pump 851, the first valve 842, and the second valve 852 (opening of the first valve and closing of the second valve);

(f) transmitting the extracted sterilant to the vaporization device 832 through the pipe 833 of the sterilant provider 830 due to the pressure difference;

(g) injecting the sterilant vaporized in the vaporizer 832 into the packaging pouch 817, due to the pressure difference, through the path 812b formed in the inner tube 831a of the needle 831 of the sterilant provider 830 and the injector 812 of the cartridge 810;

(h) sterilizing the article to be sterilized by diffusing and moving the vaporized sterilant through a space made by the tray 818 located inside the packaging pouch 817;

(i) exhausting the gas and sterilant in the packaging pouch 817 through the path 812b formed in the inner tube 831a of the needle 831 of the sterilant provider 830 and the injector 812 of the cartridge 810, according to the operations of the vacuum pump 851, the first valve 842, and the second valve 852 (the closing of the first valve and the opening of the second valve), wherein the exhausted gas and sterilant are purified through the filter 880 and discharged to the outside;

(j) repeating operations (e) to (i) using a sterilant 813*b* contained in the auxiliary sterilant container 813 when two sterilization processes are required;

(k) separating the needles 831 and 841 from the cartridge 810 by the driver 843 provided in the sterilant extractor 840 by moving the needle 841 of the sterilant extractor 840 and the needle 831 of the sterilant provider 830 in a direction opposite to the direction of the cartridge 810; and (l) separating the cartridge 810 from the coupling container 820.

A sterilization device according to a sixth embodiment of the present disclosure will be described with reference to FIG. 10. FIG. 10 is a conceptual diagram of the sterilization device according to the sixth embodiment of the present disclosure. The sterilization device 900 according to the fifth embodiment of the present disclosure includes a cartridge 910, a coupling container 920, a sterilant provider 930, a sterilant extractor 940, an intake and exhaust module 950, a heating module 960, a chamber 970, and a connection pipe 980.

The cartridge 910 includes a sterilant container 911, an injector 912, an auxiliary sterilant container 913, the coupling portion 814 (of FIG. 8), a tag 915, a body portion 916, and a packaging pouch 917. Since the cartridge is substantially the same as the cartridge 20 according to the second embodiment of the present disclosure, a detailed description of each component constituting the cartridge 910 will not be given herein.

The coupling container 920, which is configured to contain the cartridge 910 such that the cartridge 910 is located at a certain place, is fixed to the chamber 970 and coupled to the coupling portion 814 (of FIG. 8) of the cartridge 910. Since the specific configuration of the coupling container 920 is substantially the same as the coupling container 820 according to the fifth embodiment of the present disclosure, a detailed description thereof will not be given herein.

The sterilant provider 930 may include a needle 931 which may penetrate an elastic sealing material (not shown) that seals the injector 912 of the cartridge 910, a vaporizer 932 formed around the needle 931, and a pipe 933 receiving a sterilant extracted from the sterilant extractor 940.

The sterilant extractor 940 includes a needle 941 which may penetrate an elastic sealing material (not shown) that seals the sterilant container 911 of the cartridge 910, a first valve 942 for controlling a sterilant flow, and a driver 943 for moving the needle 941 in a vertical direction.

The intake and exhaust module 950 includes a vacuum pump 951, a second valve 952 for controlling the flow of gas, a third valve 955, an exhaust filter 953, and an intake filter 954. The second valve 952 is between the connection pipe 980 and the vacuum pump 951, and the third valve 955 is between the connection pipe 980 and the intake filter 954. The exhaust filter 953 is connected to the vacuum pump 951 and, when exhausting gas received from the vacuum pump 951 to the outside in a process of decompressing the inside of the packaging pouch 917 or the chamber 970, filters out harmful components in the gas. The intake filter 954 is a device for filtering harmful components or dust of air to be injected into the chamber 970.

The heating module 960 includes heaters 961 and 962 and temperature measuring devices 963 and 964. The heaters 961 and 962 are attached to upper and lower surfaces of the chamber 970 to heat the chamber 970 or the interior thereof. The temperature measuring devices 963 and 964 measure the temperature of the chamber 970 or the interior thereof so that the chamber 970 or the interior thereof may be maintained at a certain temperature.

The chamber 970 is a structure for supporting or containing the cartridge 810 and the coupling container 820, and needs to be sealed to reduce the pressure inside the chamber 970.

The connection pipe 980 includes a fourth valve 981 connected to the intake and exhaust module 950 and the chamber 970 to control the flow of gas, a fifth valve 982 connected to the intake and exhaust module 950 and the sterilant provider 930 to control the flow of gas, and a pressure sensor 983 for measuring the pressure inside the chamber 970.

The sterilization device 900 according to the sixth embodiment of the present disclosure includes:

(a) containing an article to be sterilized in the packaging pouch 917 of the cartridge 910, coupling the cartridge 910 to the coupling container 920 inside the chamber 970 of the sterilization device 900, and closing the chamber 970, wherein information about the tag 915 of the cartridge 910 is reviewed to determine whether the cartridge 910 is genuine or reused;

(b) moving the needle 941 of the sterilant extractor 940 and the needle 931 of the sterilant provider 930 in a direction of the cartridge 910 by the driver 943 provided in the sterilant extractor 940 such that the needles 931 and 941 penetrate elastic sealants (not shown) sealing the sterilant container 911 and the injector 912 of the cartridge 910, respectively, wherein the needle 931 of the sterilant provider 930 may be moved separately by a separate driving device (not shown);

(c) exhausting gas in the packaging pouch 917 to reduce the pressure through a path (not shown) formed in an inner tube (not shown) of the needle 931 of the sterilant provider 930 and the injector 912 of the cartridge 910 by the sterilant provider 930, which is connected to the vacuum pump module 950 through the fifth valve 982 of the connection pipe 980, according to operations of the vacuum pump 951 and the first to fifth valves (closing of the first valve, opening of the second valve, closing of the third valve, closing of the fourth valve, and opening of the fifth valve);

(d) exhausting gas in the chamber 970 to reduce the pressure by the chamber 970, which is connected to the intake and exhaust module 950 through the fourth valve 981 of the connection pipe 980, according to operations of the vacuum pump 951 and the first to fifth valves (closing of the first valve, opening of the second valve, closing of the third valve, opening of the fourth valve, and closing of the fifth valve), wherein operations (c) and (d) may be performed sequentially, in reverse order, or simultaneously. However, when operations (c) and (d) are performed at the same time, the vacuum pump 951 is operated to be exhausted and decompressed in a state of the first valve closed, the second valve open, the third valve closed, the fourth valve open, and the fifth valve open;

(e) operating the heating module 960 to adjust the temperature inside the chamber 970 to a set temperature, wherein the temperature control may be performed after operation (a), before operation (e), or simultaneously with other operations;

(f) extracting the sterilant (not shown) using a pressure difference through an inner tube (not shown) formed in the needle 941 of the sterilant extractor 940 by the sterilant extractor 940, which is connected to the intake and exhaust module 950 through the fifth valve 982 of the connection pipe 980, according to operations of the first valve 942 and the second valve 982 (opening of the first valve and closing of the fifth valve);

(g) transmitting the extracted sterilant to the vaporization device 932 through the pipe 933 of the sterilant provider 930 due to the pressure difference;

(h) injecting the sterilant vaporized in the vaporizer 932 into the packaging pouch 917, due to the pressure difference, through an inner tube (not shown) of the needle 931 of the sterilant provider 930 and a path (not shown) formed in the injector 912 of the cartridge 910;

(i) sterilizing an article to be sterilized by diffusing and moving the vaporized sterilant through a space in which the packaging pouch 917 is inflated due to a pressure difference between the inside and the outside;

(j) exhausting the gas and sterilant in the packaging pouch 917 through an inner tube (not shown) of the needle 931 of the sterilant provider 930 and a path (not shown) formed in the injector 912 of the cartridge 910, according to operations of the vacuum pump 951 and the first to fifth valves (closing of the first valve, opening of the second valve, closing of the third valve, closing of the fourth valve, and opening of the fifth valve), wherein the exhausted gas and sterilant are purified through the exhaust filter 953 and discharged to the outside;

(j) repeating operations (f) to (i) using a sterilant (not shown) contained in the auxiliary sterilant container 913 when two sterilization processes are required;

(k) separating the needles 931 and 941 from the cartridge 910 by the driver 943 provided in the sterilant extractor 940 by moving the needle 941 of the sterilant extractor 940 and the needle 931 of the sterilant provider 930 in a direction opposite to the direction of the cartridge 910; and (l) introducing air purified through the intake filter 954 due to a pressure difference into the chamber 970, according to operations of the first to fifth valves (closing of the first valve, closing of the second valve, opening of the third valve, opening of the fourth valve, and closing of the fifth valve); and (m) opening the chamber 970 and separating the cartridge 810 from the coupling container 820.

In the above, embodiments of the present disclosure have been described with reference to the accompanying drawings. However, the present disclosure is not limited thereto.

The invention claimed is:

1. A cartridge used for a sterilization device, the cartridge comprising:
a sterilant container configured to contain a sterilant used for sterilization;
an injector receiving the sterilant extracted from the sterilant container and delivering the sterilant to an article to be sterilized; and
a packaging pouch coupled to one end of the cartridge and containing the article to be sterilized.

2. The cartridge of claim 1, further comprising:
a coupling portion coupled to the sterilization device to induce the cartridge to be aligned in a certain position.

3. The cartridge of claim 1, wherein the packaging pouch comprises a material that does not permeate gas or liquid to maintain airtightness.

4. The cartridge of claim 1, wherein at least one surface of the packaging pouch comprises a heat conductive material.

5. The cartridge of claim 1, further comprising:
a tag for checking information about the cartridge on one side of the packaging pouch.

6. The cartridge of claim 1, further comprising:
a tray, located in the packaging pouch, for securing a space inside the packaging pouch.

7. The cartridge of claim 1, wherein the sterilant container or the injector is sealed with an elastic material.

8. The cartridge of claim 1, wherein the injector further comprises:
a path for decompressing the inside of the packaging pouch or supplying a sterilant into the packaging pouch.

9. The cartridge of claim 2, further comprising:
a tag for checking information about the cartridge on one side of the cartridge.

10. The cartridge of claim 2, wherein the sterilant container or the injector is sealed with an elastic material.

11. A cartridge used for a sterilization device, the cartridge comprising:
a sterilant container configured to contain a sterilant used for sterilization;
an injector receiving the sterilant extracted from the sterilant container and delivering the sterilant to an article to be sterilized;
a coupling portion coupled to the sterilization device to induce the cartridge to be aligned in a certain position; and
a packaging pouch containing an article to be sterilized, wherein the packaging pouch comprises a film that does not permeate gas or liquid, and one end of the packaging pouch is coupled to the cartridge so as to remain sealed.

12. A sterilization device comprising a cartridge, a sterilant extractor, and a sterilant provider, wherein the cartridge comprises:
a sterilant container configured to contain a sterilant used for sterilization;
an injector receiving the sterilant extracted from the sterilant container and delivering the sterilant to an article to be sterilized; and
a coupling portion coupled to the sterilization device to induce the cartridge to be aligned in a certain position,
wherein the sterilant extractor extracts the sterilant contained in the sterilant container and delivers the sterilant to the sterilant provider, and
the sterilant provider provides the sterilant received from the sterilant extractor to the injector.

13. The sterilization device of claim 12, further comprising:
a tag for checking information about the cartridge on one side of the cartridge.

14. The sterilization device of claim 13, wherein information about the tag is used to check whether the cartridge is in a coupled state, used, and genuine.

15. The sterilization device of claim 12, wherein the sterilant container or the injector is sealed with an elastic material.

16. The sterilization device of claim 12, further comprising:
a coupling container coupled to the coupling portion to induce the cartridge to be aligned in a certain position.

17. The sterilization device of claim 12, wherein the sterilant provider comprises a vaporizer for vaporizing and supplying a sterilant to the injector.

18. The sterilization device of claim 12, wherein the sterilant extractor comprises:
a needle for extracting a sterilant from the sterilant container, and
a driver for moving the needle.

19. The sterilization device of claim 12, further comprising:
a packaging pouch coupled to one end of the cartridge and containing the article to be sterilized.

20. The sterilization device of claim 19, wherein the packaging pouch comprises a material that does not permeate gas or liquid to maintain airtightness.

21. The sterilization device of claim 19, wherein at least one surface of the packaging pouch comprises a heat conductive material.

22. The sterilization device of claim 19, further comprising:
a tag for checking information about the cartridge on one side of the packaging pouch.

23. The sterilization device of claim 19, further comprising:
a tray, located in the packaging pouch, for securing a space inside the packaging pouch.

24. The sterilization device of claim 19, further comprising:
a heating device heating the packaging pouch or an interior space thereof.

25. The sterilization device of claim 19, further comprising:
a vacuum pump connected to the sterilant provider and decompressing the inside of the packaging pouch through the injector.

26. The sterilization device of claim 12, further comprising:
a chamber containing the cartridge therein.

27. The sterilization device of claim 26, further comprising:
a vacuum pump connected to the chamber to decompress the chamber.

28. The sterilization device of claim 26, further comprising:
a heating device heating the inside of the chamber.

29. The sterilization device of claim 26, further comprising:
a packaging pouch coupled to one end of the cartridge and containing the article to be sterilized.

30. The sterilization device of claim 29, further comprising:
a vacuum pump connected to the chamber and the sterilant provider to decompress the chamber, to decompress the inside of the packaging pouch through the injector, or to simultaneously decompress the chamber and inside of the packaging pouch through the injector.

* * * * *